(12) United States Patent
Choi

(10) Patent No.: US 10,687,782 B2
(45) Date of Patent: Jun. 23, 2020

(54) ULTRASOUND IMAGING SYSTEM WITH A TRANSMIT PULSE SEQUENCE GENERATOR CIRCUIT

(71) Applicant: MTEC GLOBAL CO., LTD., Masanhoewon-Gu, Changwon-Si (KR)

(72) Inventor: Kyusun Choi, State College, PA (US)

(73) Assignee: MTEC GLOBAL CO., LTD., Masanhoewon-Gu, Changwon-si (KR)

( * ) Notice: Subject to any disclaimer, the term of this patent is extended or adjusted under 35 U.S.C. 154(b) by 0 days.

(21) Appl. No.: 16/446,110

(22) Filed: Jun. 19, 2019

(65) Prior Publication Data

US 2019/0380675 A1  Dec. 19, 2019

Related U.S. Application Data

(60) Provisional application No. 62/686,709, filed on Jun. 19, 2018.

(51) Int. Cl.
| | |
|---|---|
| *A61B 8/06* | (2006.01) |
| *A61B 8/00* | (2006.01) |
| *A61B 8/08* | (2006.01) |
| *A61B 8/02* | (2006.01) |
| *A61B 8/14* | (2006.01) |

(52) U.S. Cl.
CPC .............. *A61B 8/06* (2013.01); *A61B 8/4444* (2013.01); *A61B 8/481* (2013.01); *A61B 8/488* (2013.01); *A61B 8/02* (2013.01); *A61B 8/0825* (2013.01); *A61B 8/14* (2013.01); *A61B 8/4483* (2013.01)

(58) Field of Classification Search
None
See application file for complete search history.

(56) References Cited

U.S. PATENT DOCUMENTS

| | | | |
|---|---|---|---|
| 9,812,216 B1 | 11/2017 | Kantipudi | |
| 2003/0028832 A1 | 2/2003 | Schaber et al. | |
| 2011/0060226 A1 | 3/2011 | Yen et al. | |
| 2013/0077445 A1 | 3/2013 | Um et al. | |
| 2019/0201074 A1* | 7/2019 | Yates | A61B 17/320068 |
| 2019/0380675 A1* | 12/2019 | Choi | A61B 8/481 |

FOREIGN PATENT DOCUMENTS

JP  2000139905 A  5/2000

OTHER PUBLICATIONS

Wygant, I. et al., Integration of 2D CMUT Arrays with Front-End Electronics for Volumetric Ultrasound Imaging, IEEE Transactions on Ultrasonics, Ferroelectrics, and Frequency Control, 55(2): 327-342, Feb. 2008.

Strickland, E., New "Ultrasound on a Chip" Tool Could Revolutionize Medical Imaging, Oct. 27, 2017. https://spectrum.ieee.org.

* cited by examiner

*Primary Examiner* — Lincoln D Donovan
*Assistant Examiner* — Khareem E Almo
(74) *Attorney, Agent, or Firm* — Dinsmore & Shohl LLP

(57) ABSTRACT

A method and apparatus of generating a sequence of pulses by a transmit signal generator. The transmit signal generator has a multiplexer that is connected to a binary counter and one of the output lines of the binary counter provides the sequence of pulses.

16 Claims, 8 Drawing Sheets

1. Continuous pulse sequence

2. Single pulse sequence

3. Two pulse sequence

4. Four pulse sequence

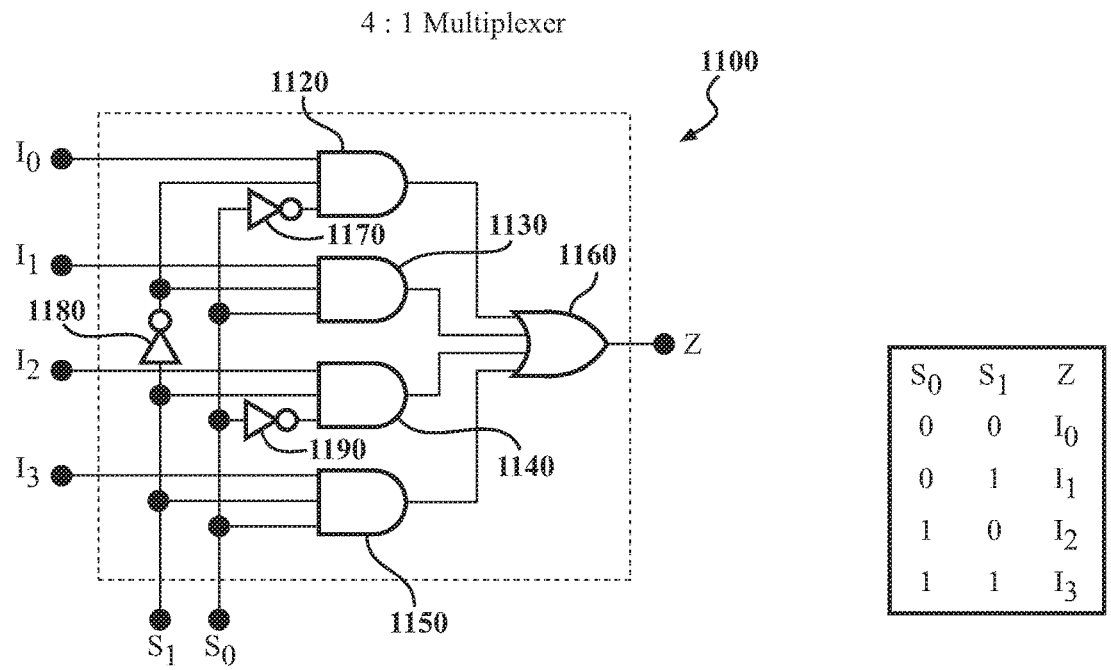
FIG. 11A    FIG. 11B
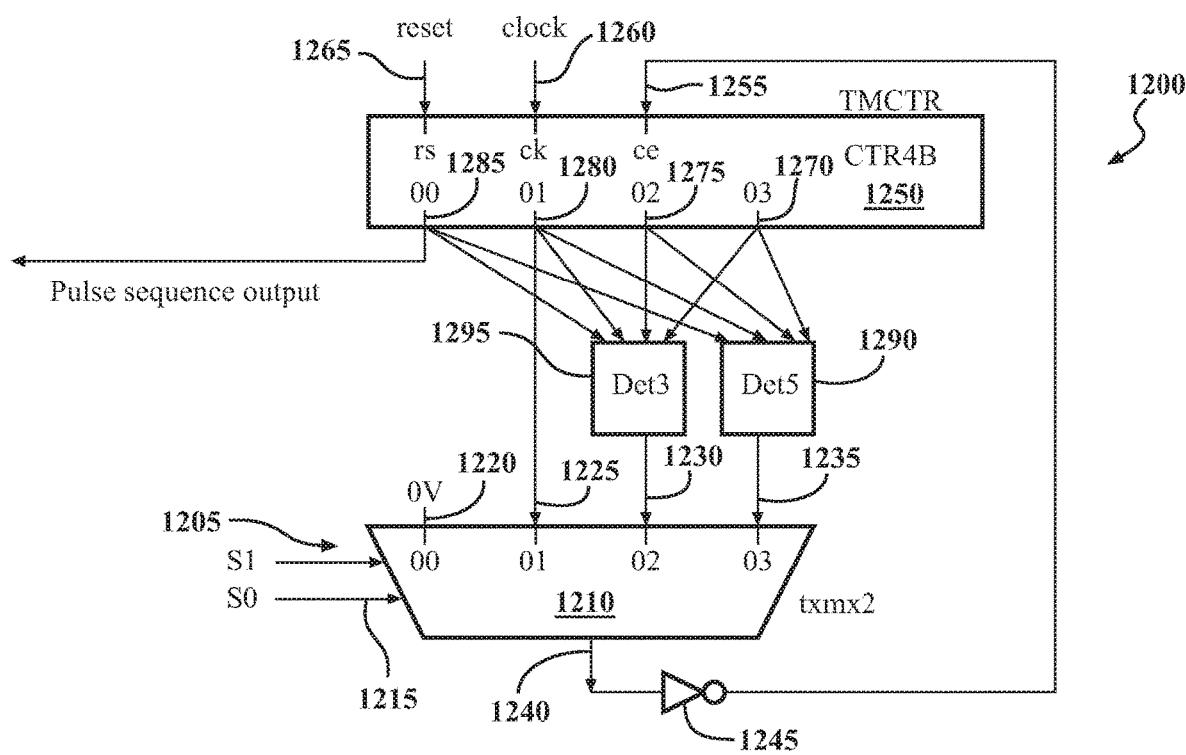
FIG. 12

(1) Detect 3 (Det3) circuit (2) Detect 5 (Det5) circuit

ULTRASOUND IMAGING SYSTEM WITH A TRANSMIT PULSE SEQUENCE GENERATOR CIRCUIT

REFERENCE TO RELATED APPLICATION

This application claims priority to U.S. Provisional Patent Application Ser. No. 62/686,709, filed Jun. 19, 2018, the entire content of which is incorporated herein by reference.

FIELD OF THE INVENTION

The present invention generally relates to the field of ultrasound imaging system with a transmit pulse sequence generator circuit.

BACKGROUND OF THE INVENTION

Ultrasound imaging (sonography) uses high-frequency sound waves to view inside the body. Because ultrasound images are captured in real-time, they can also show movement of the body's internal organs as well as blood flowing through the blood vessels. Unlike X-ray imaging, there is no ionizing radiation exposure associated with ultrasound imaging.

Ultrasound devices may be used to perform diagnostic imaging and/or treatment. Ultrasound imaging may be used to see internal soft tissue body structures. Ultrasound imaging may be used to find a source of a disease or to exclude any pathology. Ultrasound devices use sound waves with frequencies which are higher than those audible to humans.

Ultrasonic images are made by sending pulses of ultrasound into tissue using a probe. The sound waves are reflected off the tissue, with different tissues reflecting varying amounts of sound. These reflected sound waves may be recorded and displayed as an image to the operator. The strength (amplitude) of the sound signal and the time it takes for the wave to travel through the body provide information used to produce an image.

Many different types of images can be formed using ultrasound devices. The images can be real-time images. For example, images can be generated that show two-dimensional cross-sections of tissue, blood flow, motion of tissue over time, the location of blood, the presence of specific molecules, the stiffness of tissue, or the anatomy of a three-dimensional region.

In an ultrasound exam, a transducer (probe) is placed directly on the skin or inside a body opening. A thin layer of gel is applied to the skin so that the ultrasound waves are transmitted from the transducer through the gel into the body. The ultrasound image is produced based on the reflection of the waves off of the body structures. The strength (amplitude) of the sound signal and the time it takes for the wave to travel through the body provide the information necessary to produce an image.

Ultrasound imaging is a medical tool that can help a physician evaluate, diagnose and treat medical conditions. Common ultrasound imaging procedures include: Abdominal ultrasound (to visualize abdominal tissues and organs), Bone sonometry (to assess bone fragility), Breast ultrasound (to visualize breast tissue), Doppler fetal heart rate monitors (to listen to the fetal heart beat), Doppler ultrasound (to visualize blood flow through a blood vessel, organs, or other structures), Echocardiogram (to view the heart), Fetal ultrasound (to view the fetus in pregnancy), Ultrasound-guided biopsies (to collect a sample of tissue), Ophthalmic ultrasound (to visualize ocular structures, and Ultrasound-guided needle placement (in blood vessels or other tissues of interest).

Ultrasound imaging has been used for many years and has an excellent safety record. It is based on non-ionizing radiation, so it does not have the same risks as X-rays or other types of imaging systems that use ionizing radiation.

There are various ultrasound procedures that may be used to produce an ultrasound image. The choice of which type of procedure to use depends on the goals for a particular test, the phenomena being investigated and what equipment is available. The most common type of ultrasound picture is a series of flat, two-dimensional cross section images of the scanned tissue. Referred to simply as 2D ultrasound, this mode of scanning is still standard for many diagnostic and obstetric situations after a half-century of use.

In recent years, 2D ultrasound images have also been projected into three-dimensional representations. This is achieved by scanning tissue cross sections at many different angles and reconstructing the data received into a three-dimensional image. A common use for 3D ultrasound pictures is to provide a more complete and realistic image of a developing fetus. By updating 3D ultrasound images in rapid succession, sonographers can also create 4D ultrasound pictures. In the 4D ultrasound, the fourth dimension, time, adds movement and creates the most realistic representation of all.

In some cases, 3D and 4D ultrasound pictures may reveal abnormalities not readily seen using 2D ultrasound. Evaluating blood flow as it moves through blood vessels is a common component of many of the types of ultrasound. While traditional 2D ultrasound and its three-dimensional offshoot show internal tissues and structures, a different kind of ultrasound is required to evaluate blood flow and pressure within a blood vessel.

A Doppler ultrasound analysis bounces high-frequency sound waves off blood cells in motion and records changes in frequency of the sound waves as they echo back to the transducer probe. It then converts this data into a visual representation of how fast and in what direction blood is flowing. A useful diagnostic tool may be preferable in many cases to X-ray angiography because it does not require injecting the patient with contrasting dye.

Three types of Doppler ultrasound are currently in use in addition to routine grayscale imaging. Of these, color Doppler uses a wide choice of colors to visualize blood flow measurements and embed them within a conventional 2D ultrasound of tissues and structures. This provides a more pronounced representation of blood flow speed and direction than is the case with traditional grayscale images. Power Doppler provides color imaging of more sensitive and detailed blood flow measurements than regular color Doppler does. It can sometimes even achieve images in situations not accessible with color Doppler. However, power Doppler is limited in another way because it cannot indicate the direction in which blood is flowing. Like conventional and color Doppler, spectral Doppler can scan to determine both blood flow and direction but displays this data in graphic form rather than with grayscale or color images.

It is known to use a function generator for generating ultrasound frequency pulses. The basic function generator is usually a piece of electronic equipment or software used to generate different types of electrical waveforms over a wide range of frequencies. More advanced function generators, such as arbitrary waveform generators (AWG), use direct digital synthesis (DDS) techniques to generate any waveform that can be described by a table of amplitudes. Direct digital synthesis (DDS) is a method employed by frequency synthesizers used for creating arbitrary waveforms from a single, fixed-frequency reference clock. DDS is used in applications such as signal generation, local oscillators in communication systems, function generators, mixers, modulators, sound synthesizers and as part of a digital phase-locked loop.

The equipment and software currently required for generating a sequence of pulses have limitations of being complex and costly. Thus, it is desirable to provide a better solution in order to overcome limitations of the existing technologies.

SUMMARY OF THE INVENTION

A transmit signal generator for generating a sequence of pulses according to one embodiment has a $2^n$-to-1 multiplexer with $2^n$ input lines, one of the $2^n$ input lines being connected to ground or zero potential, n selector lines connected to a selector signal and an output line providing an output of the multiplexer. The multiplexer is operable to select one of the $2^n$ input lines as the output of the multiplexer based on the selector signal. The embodiment also has a $2^n$-bit binary counter with a clock signal input line connected to a clock signal input, a reset signal input line connected to a reset signal input, a clock enable line connected to the output line of the multiplexer providing the output of the multiplexer as an input signal for the clock enable line, and $2^n$ output lines. One of the $2^n$ output lines provides a sequence of pulse as an output of the transmit signal generator and the remaining $2^n$ output lines of the binary counter are each connected to one of the remaining $2^n$ input lines of the multiplexer. The output of the transmit signal generator provides a continuous pulse or an N pulse sequence as the output based on the selector signal and the reset signal input initiates generation of the sequence of pulses, wherein $N \leq 2^n$ and n is an integer.

Some embodiments of the transmit signal generator further have an inverter between the output line of the multiplexer and the clock enable line for inverting the output of the multiplexer and providing the inverted output as the input signal for the clock enable line. In some embodiments, the least significant bit of the input lines of the multiplexer is connected to ground or zero potential. In other embodiments, the least significant bit of the output lines of the binary counter provides the sequence of pulses as the output of the transmit signal generator. In some embodiments of the transmit signal generator, the value of N is 1 or x, and $x=2^n$.

In some embodiments of the transmit signal generator the selector signal is set to 00, 01, 10 and 11 respectively to provide the sequence of a continuous, single, two and four pulse output as the output of the transmit signal generator. The clock signal input for the binary counter may have a frequency of H Hz and the output of the transmit signal generator has a frequency of $H/2^n$ Hz. The binary counter may be a $2^n$-bit frequency counter with $2^n$ Toggle flip-flop (T-FF) circuits and ($2^n$-2) AND gates. In some embodiments, at least one of the T-FF circuits has a Data flip-flop (D-FF) circuit and an inverter. The T-FF circuit may have a Data flip-flop (D-FF), two inverters, two AND gates and an OR gate. In some embodiments, the transmit signal generator is configured with an ultrasound imaging system.

Another embodiment of a transmit signal generator for generating a sequence of pulses has a $2^n$-to-1 multiplexer with $2^n$ input lines, one of the $2^n$ input lines is connected to ground or zero potential, n selector lines connected to a selector signal and an output line to provide an output of the multiplexer, the multiplexer operable to select one of the $2^n$ input lines as the output of the multiplexer based on the selector signal. The embodiment also has a $2^n$ bit binary counter with a clock signal input line connected to a clock signal input, a reset signal input line connected to a reset signal input, a clock enable line connected to the output line of the multiplexer to provide the output of the multiplexer as an input signal for the clock enable line, and $2^n$ output lines.

One of the $2^n$ output lines provides a sequence of pulse as an output of the transmit signal generator and another of the $2^n$ output lines of the binary counter connected to one of the $2^n$ input lines of the multiplexer. The embodiment includes ($2^n$-2) integer-number detector circuits, each of the $2^n$ output lines of the binary counter connected to each of the integer-number detector circuit as input, each of the integer-number detector circuit having an output line connected to one of the remaining $2^n$ input lines of the multiplexer. The output of the transmit signal generator provides a continuous pulse or an N pulse sequence as the output based on the selector signal and the reset signal input initiates generation of the sequence of pulses, wherein $N \leq 2^n$, n is an integer and N is a positive integer number.

The integer-number detector circuits may have an AND gate and a plurality of inverters. The transmit signal generator may have an inverter between the output line of the multiplexer and the clock enable line for inverting the output of the multiplexer and providing the inverted output as the input signal for the clock enable line. In some embodiments of the transmit signal generator, the least significant bit of the input lines of the multiplexer is connected to ground or zero potential. The least significant bit of the output lines of the binary counter may provide the sequence of pulses as the output of the transmit signal generator.

In some embodiments, the selector signal is set to 00, 01, 10 and 11 respectively to provide the sequence of a continuous, single, three and five pulse output as the output of the transmit signal generator. The clock signal input for the binary counter may have a frequency of H Hz and the output of the transmit signal generator have a frequency of $H/2^n$ Hz. The binary counter may be a $2^n$-bit frequency counter comprising $2^n$ Toggle flip-flop (T-FF) circuits and ($2^n$-2) AND gates. The T-FF circuit may have a Data flip-flop (D-FF) circuit and an inverter. In other embodiments, the T-FF circuit has a Data flip-flop (D-FF), two inverters, two AND gates and an OR gate. In some embodiments, the transmit signal generator is configured with an ultrasound imaging system.

According to a further embodiment, a method of generating a sequence of pulses has the steps of providing a $2^n$-to-1 multiplexer that has $2^n$ input lines, n selector lines and an output line for providing an output of the multiplexer, connecting one of the $2^n$ input lines to ground or zero potential, connecting the n selector lines to a selector signal, the multiplexer selecting one of the $2^n$ input lines as the output of the multiplexer based on the selector signal, providing a $2^n$-bit binary counter having a clock signal input line, a reset signal input line, a clock enable line, and $2^n$ output lines, connecting the clock signal input line to a clock signal input and connecting the reset signal input line to a reset signal input. The method also includes connecting the clock enable line to the output line of the multiplexer for providing the output of the multiplexer as an input signal for the clock enable line, one of the $2^n$ output lines providing a sequence of pulse as an output of the transmit signal generator, connecting each of the remaining $2^n$ output lines of the binary counter to one of the remaining $2^n$ input lines of the multiplexer, wherein the output of the transmit signal generator providing a continuous pulse or an N pulse sequence as the output based on the selector signal and the reset signal input initiating generation of the sequence of pulses, wherein N≤2$^n$ and n is an integer.

Another embodiment of the method includes the steps of providing a 2$^n$-to-1 multiplexer having 2$^n$ input lines, n selector lines and an output line providing an output of the multiplexer, connecting one of the 2$^n$ input lines to ground or zero potential, connecting the n selector lines to a selector signal, the multiplexer selecting one of the 2$^n$ input lines as the output of the multiplexer based on the selector signal, providing a 2$^n$ bit binary counter having a clock signal input line, a reset signal input line, a clock enable line, and 2$^n$ output lines. The method includes connecting the clock signal input line to a clock signal input, connecting the reset signal input line to a reset signal input, connecting the clock enable line to the output line of the multiplexer providing the output of the multiplexer as an input signal for the clock enable line, one of the 2$^n$ output lines providing a sequence of pulse as an output of the transmit signal generator, connecting another of the 2$^n$ output lines of the binary counter to one of the 2$^n$ input lines of the multiplexer.

The method may further include providing (2$^n$-2) integer-number detector circuits, connecting each of the 2$^n$ output lines of the binary counter to each of the integer-number detector circuit as input, each of the integer-number detector circuit having an output line connected to one of the remaining 2$^n$ input lines of the multiplexer, wherein the output of the transmit signal generator providing a continuous pulse or an N pulse sequence as the output based on the selector signal and the reset signal input initiating generation of the sequence of pulses, wherein N≤2$^n$, n is an integer and N is a positive integer number.

These and additional features provided by the embodiments of the present disclosure will be more fully understood in view of the following detailed description, in conjunction with the drawings.

BRIEF DESCRIPTION OF THE DRAWINGS

The accompanying drawings, which are included to provide a further understanding of the invention and are incorporated in and constitute a part of this application, illustrate embodiment(s) of the invention and together with the description serve to explain the principle of the invention. In the drawings:

FIG. 10b shows a switch analogy for the 4-to-1 multiplexer in FIG. 10a;

FIG. 11a is a detailed diagram of a digital 4-to-1 multiplexer circuit;

FIG. 11b is a truth table for the circuit shown in FIG. 11b

FIG. 12 is a circuit diagram of another embodiment of the PSGC;

DETAILED DESCRIPTION OF THE INVENTION

For simplicity and clarity, the Figures of the present disclosure illustrate a general manner of construction of various embodiments. Descriptions and details of well-known features and techniques may be omitted to avoid unnecessarily obscuring the discussion of described embodiments of the present disclosure. It should be understood that the elements of the Figures are not necessarily drawn to scale, and that the dimensions of some elements may be exaggerated relative to other elements for enhancing understanding of described embodiments.

The proposed technology is discussed herewith in detail in reference to the Figures. This disclosure describes various embodiments related to a ultrasound transmit (Tx) pulse sequence generator circuit (PSGC) that generates a pulse signal with a selectable number of pulses. This circuit is compact, flexible, low-power, comparable with digital technology, easily implementable on a FPGA (Field Programmable Gate Array) chip, and can be integrated into a semiconductor chip. The PSGC takes clock signal input, reset signal input, and pulse selector inputs (s0, s1, s2, etc.). It generates a pulse sequence output (tps).

Figure 1:
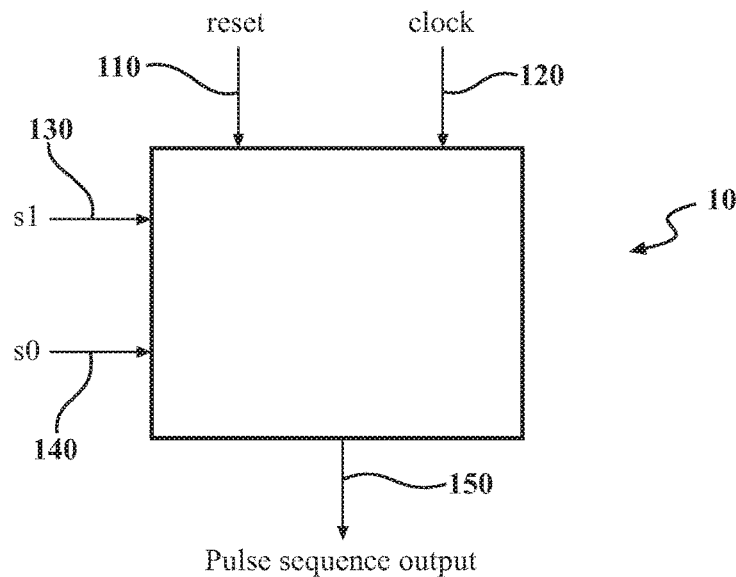
FIG. 1 is a block diagram of a pulse sequence generator circuit (PSGC)

As noted above, FIG. 1 is a block diagram of an embodiment of a pulse sequence generator circuit (PSGC) 10 according to this disclosure. Referring now to FIG. 1, the PSGC 10 takes an input clock signal 120, pulse selector inputs s1 (130) and s0 (140) and generates a pulse sequence output 150 depending on the reset signal 110. The PSGC 10 divides the input clock signal 120 by half and generates the pulse sequence output 150. For example, a 20 MHz pulse sequence output 150 is generated from a 40 MHz input clock signal and a 10 MHz pulse sequence output 150 is generated from a 20 MHz input clock signal. The reset signal 110 determines the starting of the pulse sequence output 150. In a non-limiting example, the reset signal 110 is initially active-high and when the reset signal 110 ends, the pulse sequence output 150 starts. In some embodiments, the reset signal 110 may initially be held active-low and when the reset signal 110 turns high, the pulse sequence output 150 starts.

The pulse selector inputs s1 (130) and s0 (140) determine the number of pulses present in the pulse sequence output 150. For example, the number of pulses in the pulse sequence output 150 that may be selected are 1, 2, 4, 8, etc. In one combination of the pulse selector inputs s1 (130) and s0 (140), the pulse sequence output 150 may be a continuous pulse.

Figure 2:
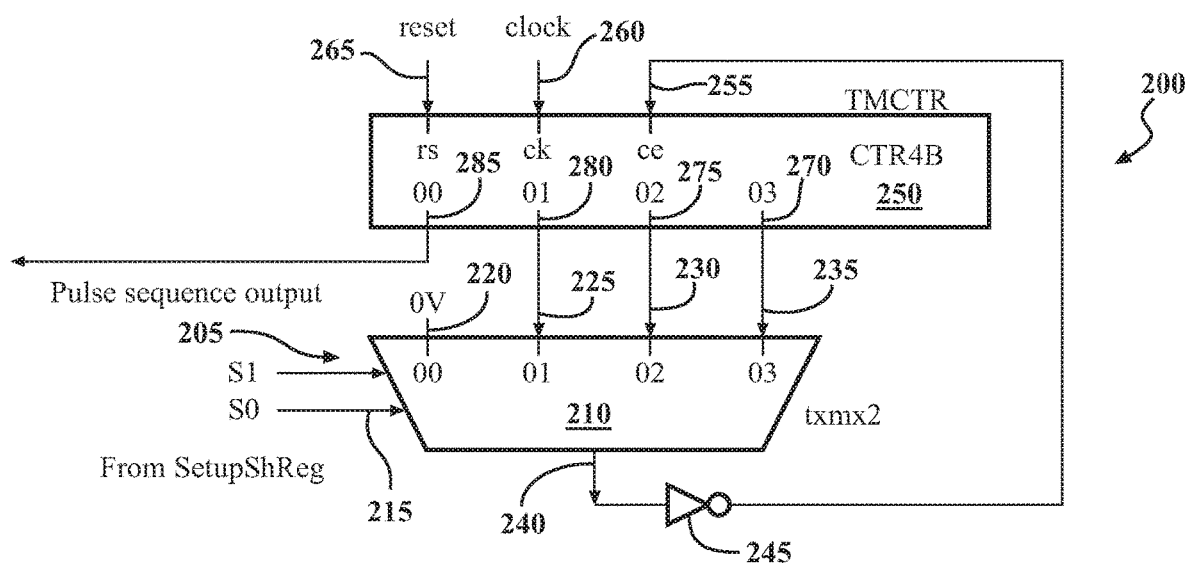
FIG. 2 shows an embodiment of a PSGC with four outputs.

As noted above, FIG. 2 shows an embodiment of a PSGC with four outputs. Referring now to FIG. 2, the PSGC 200 consist of two functional circuit modules, i.e. a 4-to-1 multiplexer 210 and a 4-bit binary counter circuit 250. In FIG. 2, the 4-to-1 multiplexer 210 is labeled as "txmx2" and the 4-bit binary counter circuit 250 is labeled as "CTR4B". The multiplexer 210 takes input signals (220, 225, 230, 235) and pulse selector inputs (205/s1, 215/s0) and generates an output signal 240.

The input signal line 220 is connected to 0V/ground/zero potential. However, it should be understood that this is merely illustrative, and the other input signal lines may instead be connected to 0V/ground/zero potential. For example, in some embodiments of the PSGC 200, the input signal line 225, 230 or 235 may be connected to 0V/ground/zero potential. The selection made by the multiplexer 210 between the input signals (220, 225, 230, 235) is determined by the pulse selector inputs (205/s1, 215/s0). Therefore, one of the input signals (220, 225, 230, 235) is selected and forwarded as the output signal 240 based on the pulse selector inputs (205/s1, 215/s0).

The counter circuit 250 takes clock enable signal "ce" 255, input clock signal 260, reset signal 265 and generates output signals 270, 275, 280 and 285. The output signal 285 provides a pulse sequence output for the PSGC 200. The remaining output signals 270, 275 and 280 respectively provide input signals 235, 230, 225 for the multiplexer 210. However, it should be understood that this is merely illustrative, and the other output signals may instead be used for providing the pulse sequence output. For example, in some embodiments of the PSGC 200, the output signals 270, 275 or 280 may provide the pulse sequence output. In that case, the remaining output signals would accordingly be connected to provide input signals for the multiplexer 210. As shown in FIG. 2, the output signal 240 of the multiplexer 210 is connected to the clock enable signal "ce" 255 through an inverter gate 245.

PSGC 200 uses a counter circuit 250 with clock enable signal "ce" as an active-high signal input. Therefore, the inverter gate 245 is required to connect the output signal 240 of the multiplexer 210 to the clock enable signal "ce" 255 through the inverter gate 245. However, it should be understood that this is merely illustrative, and other embodiments of PSGC 200 may not require the inverter gate 245. For example, a counter circuit 250 in an embodiment of PSGC 200 may present the clock enable signal "ce" as an active-low signal input, and therefore, would not require inverter gate 245.

In some embodiments, the PSGC 200 divides the input clock signal 260 by half and generates the output signal 285. For example, a 20 MHz output signal 285 is generated from a 40 MHz input clock signal 260 and a 10 MHz output signal 285 is generated from a 20 MHz input clock signal 260. The reset signal 265 determines the starting of the output signal 285. In a non-limiting example, the reset signal 265 is initially active-high and when the reset signal 265 ends, the output signal 285 starts. In some embodiments, the reset signal 265 may initially be held active-low and when the reset signal 265 turns high, the output signal 285 starts.

Figure 3:
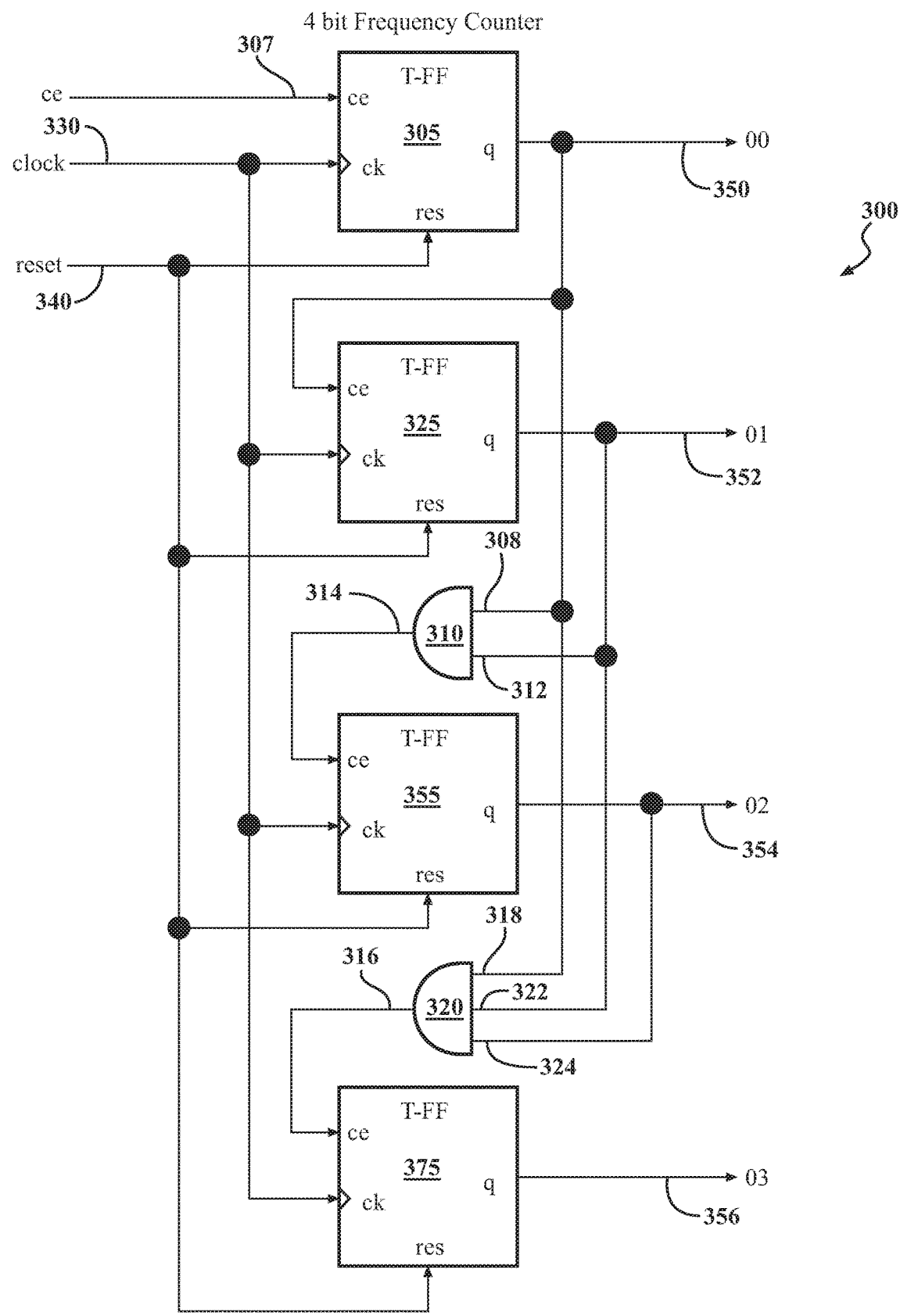
FIG. 3 is a circuit diagram of an exemplary 4-bit binary counter.

The pulse selector inputs 205 and 215 determine the number of pulses present in the output signal 285. For example, the number of pulses in the output signal 285 that may be selected are 1, 2, 4, 8, etc. In one combination of the pulse selector inputs 205 and 215, the output signal 285 may be a continuous pulse. FIG. 3 shows an exemplary 4-bit binary counter circuit that is discussed below following the discussion of FIGS. 4-7. FIGS. 4-7 show various examples of pulse signal output that may be obtained from the embodiments discussed in the present disclosure.

Figure 4:
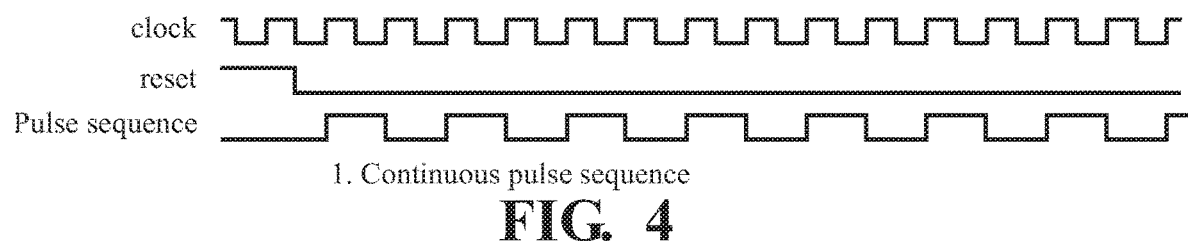
FIG. 4 shows an example of pulse signal output of the PSGC shown in FIG. 2.

FIG. 4 shows an output signal waveform for a given input clock signal and reset signal. These signals are discussed below in reference to FIG. 2. The input clock signal and reset signal of FIG. 4 may be respectively connected to the input clock signal 260 and reset signal 265 of FIG. 2. The reset signal is shown active-high, therefore when the reset signal ends, the PSGC 200 starts providing the output signal 285. If the pulse selector inputs 205, 215 are set to "00", the PSGC 200 would provide a continuous pulse output signal as shown in FIG. 4. The continuous pulse output signal is selected if all the pulse selector inputs are logic "low". The frequency of the continuous output pulse is about half the frequency of the given clock signal. If instead of input signal 220, the other input signal 225, 230 or 235 is connected to 0V, when the pulse selector inputs select 225, 230 or 235 then the output signal 285 would be a continuous output pulse.

Figure 5:
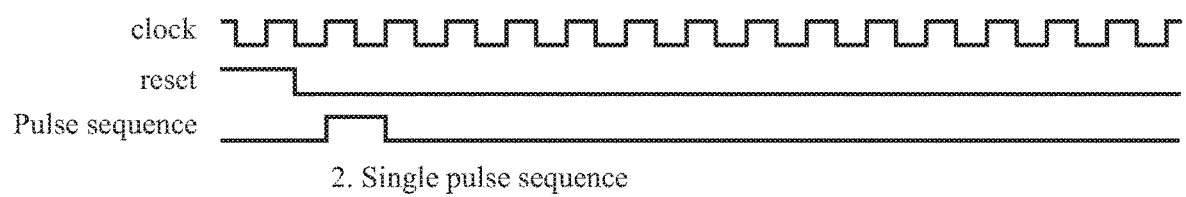
FIG. 5 also shows an example of pulse signal output of the PSGC shown in FIG. 2.

Referring to FIG. 5, another example of the output signal form for a given input clock signal and reset signal is shown. These signals are discussed below in reference to FIG. 2. The input clock signal and reset signal of FIG. 5 may be respectively connected to the input clock signal 260 and reset signal 265 of FIG. 2. The reset signal is shown active-high, therefore when the reset signal ends, the PSGC 200 starts providing the output signal 285. If the pulse selector inputs 205, 215 are set to "01", the PSGC 200 would provide a single pulse output signal as shown in FIG. 5. The frequency of the single output pulse is about half the frequency of the given clock signal.

Figure 6:
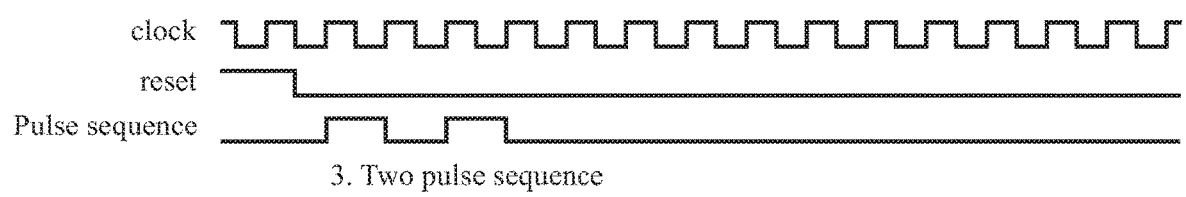
FIG. 6 shows another example of pulse signal output of the PSGC shown in FIG. 2.

Referring to FIG. 6, another example of the output signal form for a given input clock signal and reset signal is shown. These signals are discussed below in reference to FIG. 2. The input clock signal and reset signal of FIG. 6 may be respectively connected to the input clock signal 260 and reset signal 265 of FIG. 2. The reset signal is shown active-high, therefore when the reset signal ends, the PSGC 200 starts providing the output signal 285. If the pulse selector inputs 205, 215 are set to "10", the PSGC 200 would provide a two pulse output signal as shown in FIG. 6. The frequency of the two pulse output signal is about half the frequency of the given clock signal.

Figure 7:
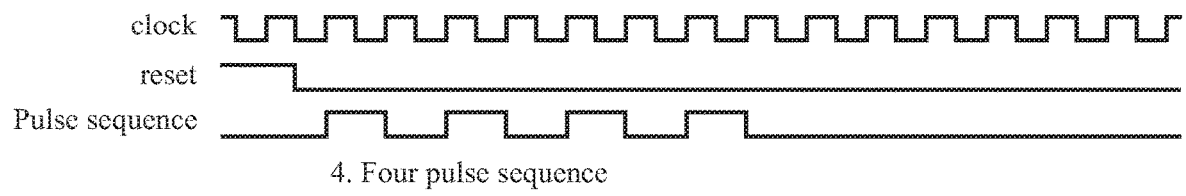
FIG. 7 shows yet another example of pulse signal output of the PSGC shown in FIG. 2.

Referring to FIG. 7, yet another example of the output signal form for a given input clock signal and reset signal is shown. These signals are discussed below in reference to FIG. 2. The input clock signal and reset signal of FIG. 7 may be respectively connected to the input clock signal 260 and reset signal 265 of FIG. 2. The reset signal is shown active-high, therefore when the reset signal ends, the PSGC 200 starts providing the output signal 285. If the pulse selector inputs 205, 215 are set to "11", the PSGC 200 would provide a four pulse output signal as shown in FIG. 7. The frequency of the four pulse output signal is about half the frequency of the given clock signal.

In a variation of the PSGC 200 in FIG. 2, the output signals 280, 270 of the counter circuit 250 may instead provide the input signals 235, 225 of the multiplexer 210. In that case, if the pulse selector inputs 205, 215 are set to "01", the PSGC 200 would provide a four pulse output signal as shown in FIG. 7. If the pulse selector inputs 205, 215 are set to "11", the PSGC 200 would provide a single pulse output signal as shown in FIG. 5. In another variation, if the output signal 280 provides the pulse sequence output for the PSGC 200, then the output pulse will be 10 MHz given that the input clock signal 260 for the counter circuit is 40 MHz. However, the remaining pulse sequence output would be limited to single pulse, two pulse and continuous pulse output signals. In general, one may use larger binary counters such as a CTR5B or CTR6B, among others, and also the larger size multiplexers such as a txmx3 or txmx4, among others, for more selection options.

As noted above, FIG. 3 shows the 4-bit binary counter circuit that may be used in embodiments of the PSGC disclosed in the present disclosure, for example, in the PSGC 10 and 200 shown respectively in FIGS. 1 and 2. The counter circuit 300 consists of four Toggle flip-flop (T-FF) circuits (305, 325, 355, 375) and two AND gates (310, 320). However, it should be understood that this is merely illustrative, and the counter circuit may have a different number of T-FF circuits and AND gates. For example, an arbitrary n-bit binary counter circuit can be constructed with n T-FF circuits and ($2^n$-2) AND gates.

Each of the T-FF circuits (305, 325, 355, 375) takes clock enable signal "ce", input clock signal "ck", reset signal "res" and generates output signal "q". In a T-FF, if the T input is high, the T-FF changes states (i.e. toggles) whenever the clock input is strobed. However, if the T input is low, the T-FF holds the previous value. Moreover, when T is held high, the T-FF divides the input clock frequency by two. For example, if the clock frequency is 40 MHz, the output frequency obtained from the T-FF is 20 MHz. Clock signal 330 and reset signal 340, respectively, provide input clock signal "ck" and reset signal "res" for all the four T-FF circuits (305, 325, 355, 375).

Enable signal 307 provides clock enable signal "ce" for the T-FF 305. When the enable signal 307 is high, the T-FF 305 generates an output signal 00 350. The output signal 00 350 is provided as an input to the clock enable signal "ce" of T-FF 325 and the AND gates 310, 320. Once T-FF 325 is enabled, T-FF 325 generates an output signal 01 352. The output signal 01 352 is provided as an input to both the AND gates 310, 320. The output 314 of the AND gate 310 is provided as an input to the clock enable signal "ce" of T-FF 355. Once T-FF 355 is enabled, T-FF 355 generates an output signal 02 354. The output signal 02 354 is provided as an input to the AND gate 320, which then generates an output 316. The output 316 is provided as an input to the clock enable signal "ce" of T-FF 375. Once T-FF 375 is enabled, T-FF 375 generates an output signal 03 356.

FIG. 3 is discussed below in reference to FIG. 2. In a non-limiting embodiment of PSGC 200, the 4-bit binary counter circuit 300 shown in FIG. 3 may be used as the counter circuit 250 of FIG. 2. In that case, enable signal 307, clock signal 330, reset signal 340, output signal 00 350, output signal 01 352, output signal 02 354 and output signal 03 356 of counter circuit 300, respectively, are equivalent to the enable signal 255, input clock signal 260, reset signal 265, and output signals 285, 280, 275, 270 of the 4-bit binary counter circuit 250 shown in FIG. 2.

Figure 8:
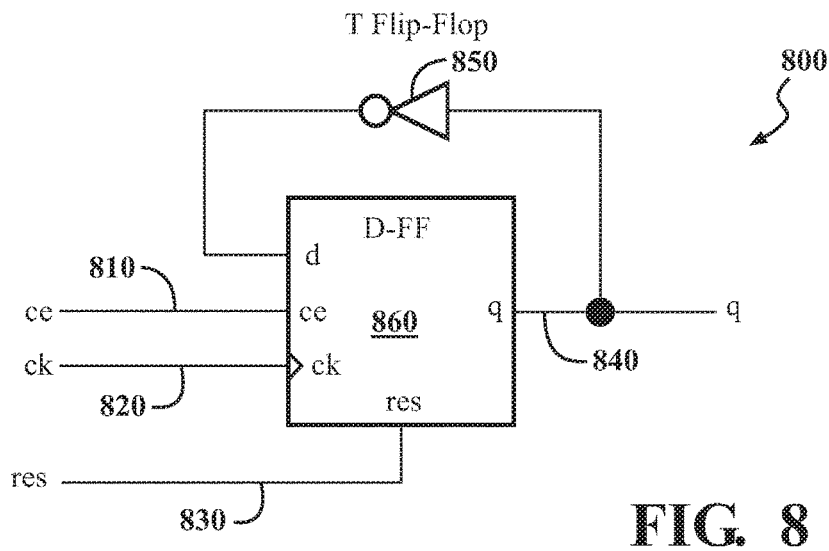
FIG. 8 is a circuit diagram of an example of Toggle flip-flop (T-FF) circuit.

FIG. 8 shows a Toggle flip-flop (T-FF) circuit 800 that may be used as one or more of the T-FF circuits (305, 325, 355, 375) used in the counter circuit 300 of FIG. 3. The T-FF 800 consists of a Data flip-flop (D-FF) circuit 860 and an inverter 850. D-FF 800 takes clock enable signal 810, input clock signal 820, reset signal 830 and data signal to provide an output q 840. The output q 840 is used as the data signal after inverting the signal using the inverter 850.

Figure 9:
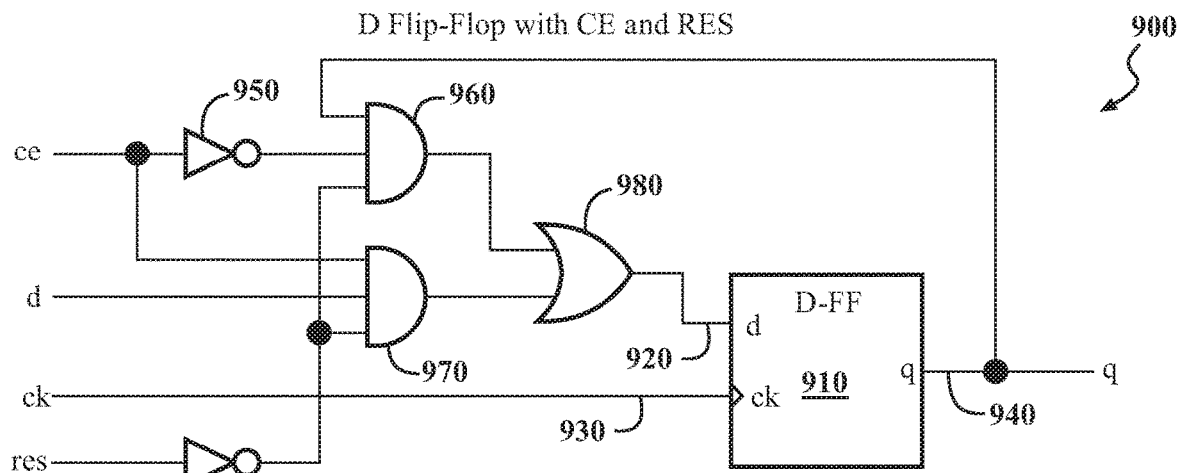
FIG. 9 is a circuit diagram of an example of Data flip-flop (D-FF) circuit.

FIG. 9 shows an exemplary design circuit of a Data flip-flop (D-FF) 900 with "ce" and "res" inputs. The D-FF circuit 900 consists of a D-FF 910, two inverters (950, 990), two AND gates (960, 970) and an OR gate 980. As shown, D-FF circuit 900 with "ce" and "res" inputs, subsequently, is built with a D-FF 910 having only data input "d" 920 and input clock signal "ck" 930. A clock enable signal "ce" acts as an input for the inverter 950 and the AND gate 970. The data signal "d" acts as one of the inputs for AND gate 970. D-FF 910 receives the input clock signal "ck" at 930. Reset signal "res" is inverted by the inverter 990 and the inverted reset signal acts as an input for the AND gates 960, 970. Outputs from AND gates 960, 970 is provided as the input to the OR gate 980. The output of the OR gate 980 is provided as data signal "d" at 920 of D-FF 910. The D-FF generates an output q 940 that also acts as an input for the AND gate 960. The reset signal "res" is a synchronous input signal in this case. However, the T-FF circuit used in a binary counter circuit may be made with an asynchronous reset signal. The asynchronous reset signal is typically called a "clear" signal instead of a reset signal. A simpler D-FF circuit discussed above, with only "d" and "ck" inputs, can be positive edge-triggered or negative edge-triggered. Consequently, the T-FF circuit used in a binary counter circuit can be positive edge-triggered or negative edge-triggered.

Figure 10A:
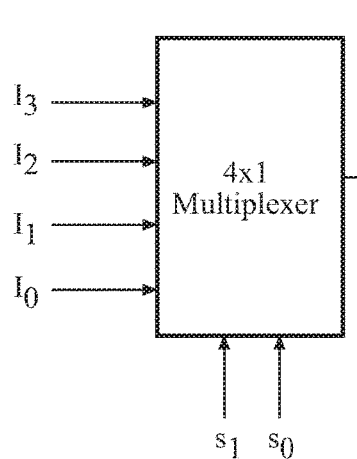
FIG. 10a is a circuit diagram of a digital 4-to-1 multiplexer.
Figure 10B:
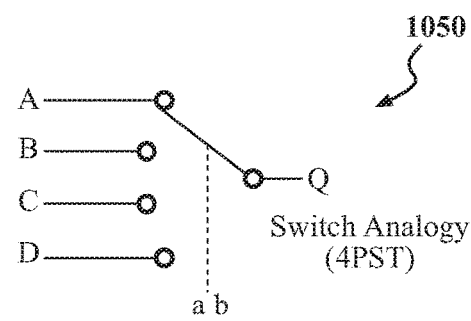

A multiplexer is a switch to select one of several analog or digital input signals and pass the selected input signal to a single output line. A multiplexer of $2^n$ inputs has n select lines, which are used to select which input line to send to the output line. The multiplexer can be considered as a multiple-input, single output switch. A circuit diagram of an example of a 4-to-1 multiplexer is shown in FIG. 10a. The 4-to-1 multiplexer 1010 has four inputs ($I_3$, $I_2$, $I_1$, $I_0$) and two selector lines ($s_1$, $s_0$). The 4-to-1 multiplexer 1010 selects one of the four inputs based on the selector lines and connects the selected line to the output line Y. FIG. 10b shows a switch analogy of a digital multiplexer. FIG. 10b shows a four-pole single-throw (4PST) switch, four inputs (A, B, C, D), an output Q and a movable link ab. One of the four inputs (A, B, C, D) is connected to the output line Q based on the position of the movable link ab.

There are many ways to implement a 4-to-1 multiplexer 1010. FIG. 11a is an exemplary detailed diagram of a digital 4-to-1 multiplexer circuit. The 4-to-1 multiplexer 1110 consists of four AND gates (1120, 1130, 1140, 1150), three inverters (1170, 1180, 1190) and an OR gate 1160. The 4-to-1 multiplexer 1110 has four inputs ($I_0$, $I_1$, $I_2$, $I_3$), two selector inputs ($S_1$, $S_0$) and provides an output Z based on the selectors input. Each of the inputs $I_0$, $I_1$, $I_2$, $I_3$ is connected respectively to the AND gates 1120, 1130, 1140, 1150. Selector input $S_1$ is connected to the AND gates 1140, 1150. Selector input $S_1$ is inverted using inverter 1180 and the output of the inverter 1180 is connected to the AND gates 1120, 1130. Selector input $S_0$ is connected to the AND gates 1130, 1150. Selector input $S_0$ is inverted using inverter 1190 and the inverted input is connected to the AND gate 1190. Similarly, selector input $S_0$ is inverted using inverter 1170 and the inverted input is connected to the AND gate 1120. Outputs from all the four AND gates (1120, 1130, 1140, 1150) are connected to the OR gate that provides Z as the output.

FIG. 11b also shows a truth table for the 4-to-1 multiplexer 1110. For example, the state of selector inputs ($S_0$, $S_1$) as 00, 01, 10, 11 respectively provides $I_0$, $I_1$, $I_2$, $I_3$ as output Z. However, it should be understood that this is merely illustrative, and a PSGC may consist of multiplexers with more inputs than the 4-to-1 multiplexer 1110.

As noted above, the number of pulses in the pulse sequence output generated by the PSGC 200 can be 1, 2, 4, 8, 16 etc. The number of pulses generated in the sequence is in power of two number, except for the continuous pulse sequence. Another embodiment of the PSGC is shown in FIG. 12. The PSGC 1200 shown in FIG. 12 is similar to the PSGC 200 but also has two integer-number detector circuits (i.e. number 3 detector circuit "det3" 1295 and number 5 detector circuit "det5" 1290). The resulting PSGC 1200 is capable of generating 1, 3, 5 and continuous pulse sequences. A PSGC according to this disclosure may use a plurality of integer-number detector circuits. The integer-number detector circuits enable a PSGC to generate an integer-numbered pulse sequence output. In non-limiting integer-number detector circuit examples (not shown), a number 7 detector circuit, a number 9 detector circuit and a number 11 detector circuit if used in the PSGC according to this disclosure would respectively enable it to generate 7, 9 and 11 pulse sequence output.

As noted above, FIG. 12 shows the embodiment of a PSGC with four outputs. Referring now to FIG. 12, the PSGC 1200 consist of four functional circuit modules, i.e. a 4-to-1 multiplexer 1210, a 4-bit binary counter circuit 1250 and two integer-number detector circuits det3, det5. In FIG. 12, the 4-to-1 multiplexer 1210 is labeled as "txmx2" and the 4-bit binary counter circuit 250 is labeled as "CTR4B". The multiplexer 1210 takes input signals (1220, 1225, 1230, 1235) and pulse selector inputs (1205/s1, 1215/s0) and generates an output signal 1240.

The input signal 1220 is connected to 0V/ground/zero potential. However, it should be understood that this is merely illustrative, and the other input signals may instead be connected to 0V/ground/zero potential. For example, in some embodiments of the PSGC 1200, the input signal 1225, 1230 or 1235 may be connected to 0V/ground/zero potential. The selection made by the multiplexer 1210 between the input signals (1220, 1225, 1230, 1235) is determined by the pulse selector inputs (1205/s1, 1215/s0). Therefore, one of the input signals (1220, 1225, 1230, 1235) is selected and forwarded as the output signal 1240 based on the pulse selector inputs (1205/s1, 1215/s0).

The counter circuit 1250 takes clock enable signal "ce" 1255, input clock signal 1260, reset signal 1265 and generates output signals 1270, 1275, 1280 and 1285. The output signal 1285 provides a pulse sequence output for the PSGC 1200. All the output signals 1270, 1275, 1280 and 1285 provide input signals for the det3 and det5. In addition, the output signal 1280 provides an input signal 1225 for the multiplexer 1225. Outputs from det3 and det5 respectively are provided as input signals 1230 and 1235 for the multiplexer 1210. However, it should be understood that this is merely illustrative, and the other output signals may instead be used for providing the pulse sequence out. For example, in some embodiments of the PSGC 1200, the output signals 1270, 1275 or 1280 may provide the pulse sequence output. In that case, the remaining connections between the counter circuit 1250, det3, det5 and the multiplexer 1210 remain unchanged. As shown in FIG. 12, the output signal 1240 of the multiplexer 1210 is connected to the clock enable signal "ce" 1255 through an inverter gate 1245.

The PSGC 1200 uses a counter circuit 1250 with the clock enable signal "ce" as an active-high signal input. Therefore, the inverter gate 1245 is required to connect the output signal 1240 of the multiplexer 1210 to the clock enable signal "ce" 1255 through the inverter gate 1245. However, it should be understood that this is merely illustrative, and other embodiments of the PSGC 1200 may not require the inverter gate 1245. For example, a counter circuit 1250 in an embodiment of the PSGC 1200 may present the clock enable signal "ce" as an active-low signal input, and therefore, would not require the inverter gate 1245.

In some embodiments, the PSGC 1200 divides the input clock signal 1260 by half and generates the output signal 1285. For example, the 20 MHz output signal 1285 is generated from the 40 MHz input clock signal 1260 and the 10 MHz output signal 1285 is generated from the 20 MHz input clock signal 1260. The reset signal 1265 determines the starting of the output signal 1285. In a non-limiting example, the reset signal 1265 is initially active-high and when the reset signal 1265 ends, the output signal 1285 starts. In some embodiments, the reset signal 1265 may initially be held active-low and when the reset signal 1265 turns high, the output signal 1285 starts.

The pulse selector inputs 1205 and 1215 determine the number of pulses present in the output signal 1285. For example, the number of pulses in the output signal 1285 that may be selected are 1, 3, 5, etc. In one combination of the pulse selector inputs 1205 and 1215, the output signal 1285 may be a continuous pulse. As discussed above, FIG. 3 shows an exemplary 4-bit binary counter circuit. FIGS. 4-5 show two examples of a pulse signal output that may be obtained from the embodiments discussed in the present disclosure.

FIG. 4 shows an output signal waveform for a given input clock signal and reset signal. These signals are discussed below in reference to FIG. 12. The input clock signal and reset signal of FIG. 4 may be respectively connected to the input clock signal 1260 and reset signal 1265 of FIG. 12. The reset signal is shown active-high, therefore when the reset signal ends, the PSGC 1200 starts providing the output signal 1285. If the pulse selector inputs 1205, 1215 are set to "00", the PSGC 1200 would provide a continuous pulse output signal as shown in FIG. 4. The continuous pulse output signal is selected if all the pulse selector inputs are logic "low". The frequency of the continuous output pulse is about half the frequency of the given clock signal. If instead of the input signal 1220, the other input signal 1225, 1230 or 1235 is connected to 0V, when the pulse selector inputs select 1225, 1230 or 1235 then the output signal 1285 would be a continuous output pulse.

Referring to FIG. 5, another example of the output signal form for a given input clock signal and reset signal is shown. These signals are discussed below in reference to FIG. 12. The input clock signal and reset signal of FIG. 5 may be respectively connected to the input clock signal 1260 and reset signal 1265 of FIG. 12. The reset signal is shown active-high, therefore when the reset signal ends, the PSGC 1200 starts providing the output signal 1285. If the pulse selector inputs 1205, 1215 are set to "01", the PSGC 1200 would provide a single pulse output signal as shown in FIG. 5. The frequency of the single output pulse is about half the frequency of the given clock signal.

The input clock signal and reset signal may be respectively connected to the input clock signal 1260 and reset signal 1265 of FIG. 12. If the reset signal is active-high, and the reset signal ends, the PSGC 1200 starts providing the output signal 1285. If the pulse selector inputs 1205, 1215 are set to "10", the PSGC 1200 would provide a three pulse output signal (not shown). The frequency of the single output pulse is about half the frequency of the given clock signal.

Similarly, the input clock signal and reset signal may be respectively connected to the input clock signal 1260 and reset signal 1265 of FIG. 12. If the reset signal is active-high, and the reset signal ends, the PSGC 1200 starts providing the output signal 1285. If the pulse selector inputs 1205, 1215 are set to "11", the PSGC 1200 would provide a three pulse output signal (not shown). The frequency of the single output pulse is about half the frequency of the given clock signal.

In a variation of the PSGC 1200 in FIG. 12, the output signal 1280 and output from det5 may instead provide the input signals 1235, 1225 of the multiplexer 1210. In that case, if the pulse selector inputs 1205, 1215 are set to "01", the PSGC 200 would provide a five pulse output signal (not shown). If the pulse selector inputs 1205, 1215 are set to "11", the PSGC 1200 would provide a single pulse output signal as shown in FIG. 5. In another variation, if the output signal 1280 provides the pulse sequence output for the PSGC 1200, then the output pulse will be 10 MHz given that the input clock signal 1260 for the counter circuit is 40 MHz. However, the remaining pulse sequence output would be limited to single pulse, three pulse and continuous pulse output signals. In general, one may use larger binary counters such as a CTR5B or CTR6B, among others, and also the larger size multiplexers such as a txmx3 or txmx4, among others, for more selection options. According to this disclosure, the number of pulses in the output pulse sequence in the PSGC 200 and the PSGC 1200 are dynamically selectable from the predetermined set of options.

Figure 13:
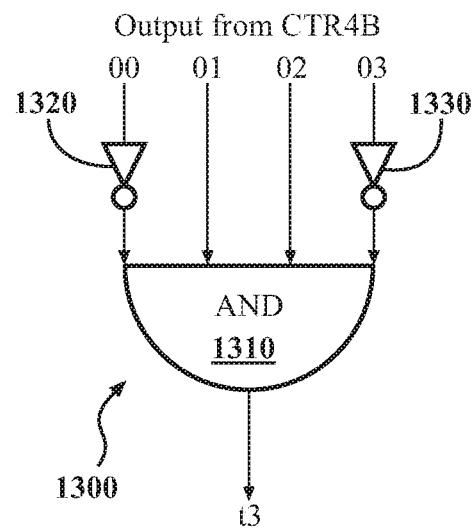
FIG. 13 is a detector circuit diagram.

FIG. 13 shows an integer-number detector circuit det3 1300 that may be used in the PSGC 1200 shown in FIG. 12. The det3 1300 consists of a 4-input AND gate 1310 and two inverters 1320, 1330. An AND gate 1310 receives four inputs 00, 01, 02, 03 and provides an output t3. The inputs 00 and 03 are first inverted using the inverters 1320, 1330 respectively before being used as inputs for the AND gate 1310. FIG. 13 is discussed below in reference to FIG. 12. If the det3 1300 is used in the PSGC 1200, the output t3 may provide an input 1230 for the multiplexer 1210. The output signals 1270, 1275, 1280, 1285 of the counter circuit 1250 are respectively connected as inputs 03, 02, 01, 00 of the det3 1300. The integer-number detector circuit det3 1300 would enable the PSGC 1200 to generate a three pulse sequence output. It should be understood that this is merely illustrative, and the other components/gates or their combination may instead be used to execute similar signal processing.

In FIG. 13, the det3 circuit provides an output t3=(not 00), (01), (02) and (not 03). In other words, det3 enables generating a three-pulse output sequence. This may be changed to det4 circuit (not shown) if the output t3=(not 00), (not 01), (not 02) and (03). Alternatively, det3 may be changed to det5 if the output t3=(not 00), (01), (not 02) and (03). Det3 may also be changed to det6 if t3=(not 00), (not 01), (02) and (03). In some embodiments, det3 may be changed to det7 if t3=(not 00), (01), (02) and (03). The PSGC 1200 may generate any positive integer number of pulses, if different combinations of the det circuits are used. In some embodiments of the PSGC, an odd number and/or an even number of pulses may be generated as the output pulse sequence. The PSGCs disclosed herein may be configured for generating continuous pulses as well as any positive integer number of pulses as an output sequence.

Figure 14:
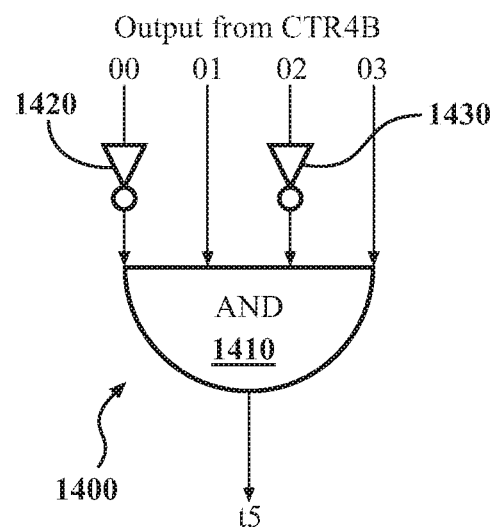
FIG. 14 is another detector circuit diagram.

FIG. 14 shows an integer-number detector circuit det5 1400 that may be used in the PSGC 1200 shown in FIG. 12. The det5 1400 consists of a 4-input AND gate 1410 and two inverters 1420, 1430. An AND gate 1410 receives four inputs 00, 01, 02, 03 and provides an output t5. The inputs 00 and 02 are first inverted using the inverters 1420, 1430 respectively before being used as inputs for the AND gate 1410. FIG. 14 is discussed below in reference to FIG. 12. If the det5 1400 is used in the PSGC 1200, the output t5 may provide an input 1235 for the multiplexer 1210. The output signals 1270, 1275, 1280, 1285 of the counter circuit 1250 are respectively connected as inputs 03, 02, 01, 00 of the det5 1400. The integer-number detector circuit det5 1400 would enable the PSGC 1200 to generate a five pulse sequence output. It should be understood that this is merely illustrative, and the other components/gates or their combination may instead be used to execute similar signal processing.

Figure 15:
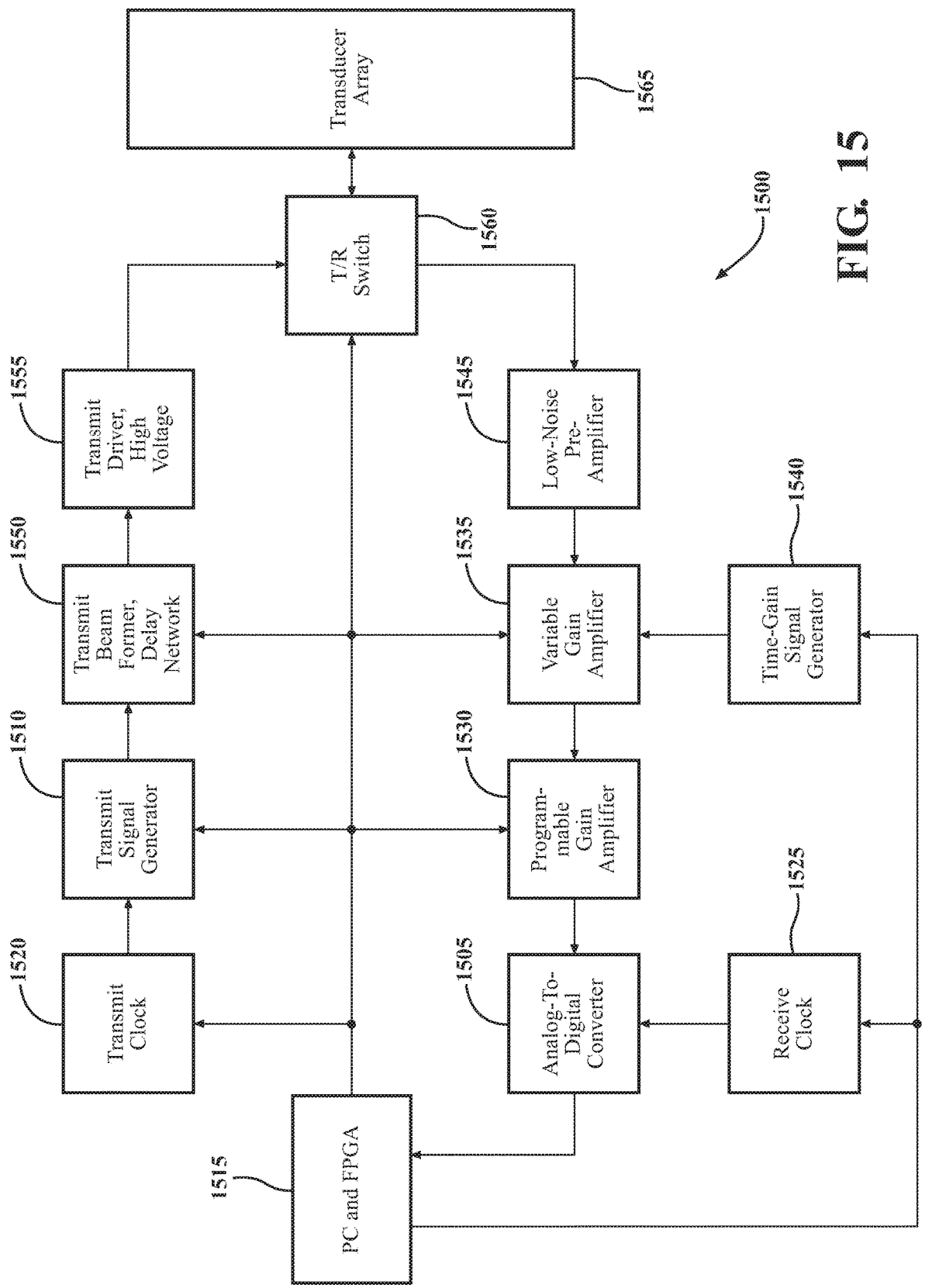
FIG. 15 is a block diagram of an ultrasound imaging system.

There are many applications for the embodiments of a PSGC as disclosed herein. The proposed technology is discussed herewith in detail in reference to an ultrasound probe. However, it should be understood that this is merely illustrative, and the proposed technology has other applications and uses. Non-limiting examples include a general purpose trigger signal generator, general purpose pulse burst generator, one-shot timer, strobe light etc. FIG. 15 is a block diagram of an ultrasound imaging system 1500, wherein the above discussed embodiments of the PSGC may be used as signal generator. It should be noted that the ultrasound imaging system 1500 is discussed herein for illustration and the ultrasound imaging system using the PSGC may have more, less or alternative components than those shown in FIG. 15.

The ultrasound imaging system 1500 measures the reflectivity of tissue to sound waves. It can also measure velocity of moving objects, e.g. blood flow. The system 1500 provides a non-invasive imaging system without exposing a person to any radiation. The system 1500 consists of a transducer array 1565 that is used both as a transmitter and a receiver. In a transmission mode, the transmitter converts an oscillating voltage into mechanical vibrations, which transmits a series of sound pressure waves into the body. In a receiving mode, the receiver converts backscattered sound pressure waves into electrical signals. In a non-limiting example, the transducer array 1565 is comprised of an array of piezoelectric transducer elements that transmit focused energy into the body and receive the resulting reflections. The transducer array 1565 may have 32 to as many as 512 elements and may operate at frequencies from 1 MHz to 15 MHz.

The ultrasound imaging system 1500 also has a transmitter/receiver (T/R) switch 1560. As noted above, the transducer array 1565 may have 32 to as many as 512 elements, but the system may have fewer transmitters and receivers than the number of available transducer elements. In these cases, a T/R switch 1560 located in the system 1500 is used as multiplexer to connect a specific transducer element to a specific transmitter/receiver pair.

The ultrasound imaging system 1500 also has a Personal Computer and Field Programmable Gate Array (PC/FPGA) 1515 with one or more microprocessors that directs the operation of the entire system. The PC 1515 senses the settings of the controls and input devices, such as the keyboard, and executes the commands to control the hardware to function in the desired mode. It orchestrates the necessary setup of the transmit and receive beamformers 1550 as well as the signal processing, display, and output functions. Another important duty of the computer is to regulate and estimate the level of acoustic output in real time.

The ultrasound imaging system 1500 also has a transmit clock 1520 that provides an input clock signal for various components of the system 1500. As discussed above, the PSGC 200 and 1200 both respectively receive input clock signals 260 and 1260. The transmit clock 1520 provides an input signal to the transmit signal generator 1510. Various embodiments of the transmit signal generators (i.e. PSGC 200 and 1200) are discussed above.

The transmit signal generator 1510 transmits its output signal to a transmit beamformer 1550 that typically generates the necessary digital transmit signals with the proper timing and phase to produce a focused transmit signal. The ultrasound imaging system 1500 may generate complex transmit waveforms using an arbitrary waveform generator to optimize image quality. In these cases, the transmit beamformer 1550 may generate digital 8-bit to 10-bit words at rates of approximately 40 MHz to produce the required transmit waveform.

A high-voltage transmit driver 1555 conditions the transmit waveform from the transmit beamformer 1550 and transmits the conditioned transmit waveform to the T/R switch 1560. As discussed above, a T/R switch 1560 located in the system 1500 connects a specific transducer element to a specific transmitter/receiver pair.

The T/R switch 1560 is connected to a Low Noise Pre-Amplifier (LNA) 1545. It is desirable that the LNA 1545 have excellent noise performance and sufficient gain. The transducer element from the transducer array 1565 may be directly/indirectly connected to the LNA 1545 through a relatively long coaxial transducer cable terminated into relatively low impedance at the LNA's 1545 input. The signal received from the transducer array 1565 is amplified by the LNA 1545 and later conditioned by a variable gain amplifier 1535 and a programmable gain amplifier 1530.

During the ultrasound send-receive cycle, the magnitude of reflected signal depends on the depth of penetration. The purpose of Time Gain Control (TGC) is to normalize the signal amplitude with time; compensating for depth. When the image is displayed, similar material should have similar brightness, regardless of depth and this is achieved by "Linear-in-dB" Gain, which means the decibel gain is a linear function of the control voltage. A time gain signal generator 1540 is connected to variable gain amplifier 1535 for TGC.

The signal from the programmable gain amplifier 1505 is then transmitted to an analog to digital converter to convert the analog amplified received signal into a digital format for further processing to the PC 1515. The analog to digital converter 1505 receives an input from a receive clock 1525. Various components of the ultrasound imaging system 1500 are connected to the PC 1515 and are not discussed in detail here.

Additional features and functionality of the ultrasound imaging system 1500 should generally be understood and are not discussed in further detail herein. Additionally, it should be understood that the various components described with respect to the transmit signal generator are merely illustrative. Accordingly, the ultrasound imaging system 1500 may include additional components, fewer components, alternative components, and/or the like without departing from the scope of the present disclosure.

Figure 16:
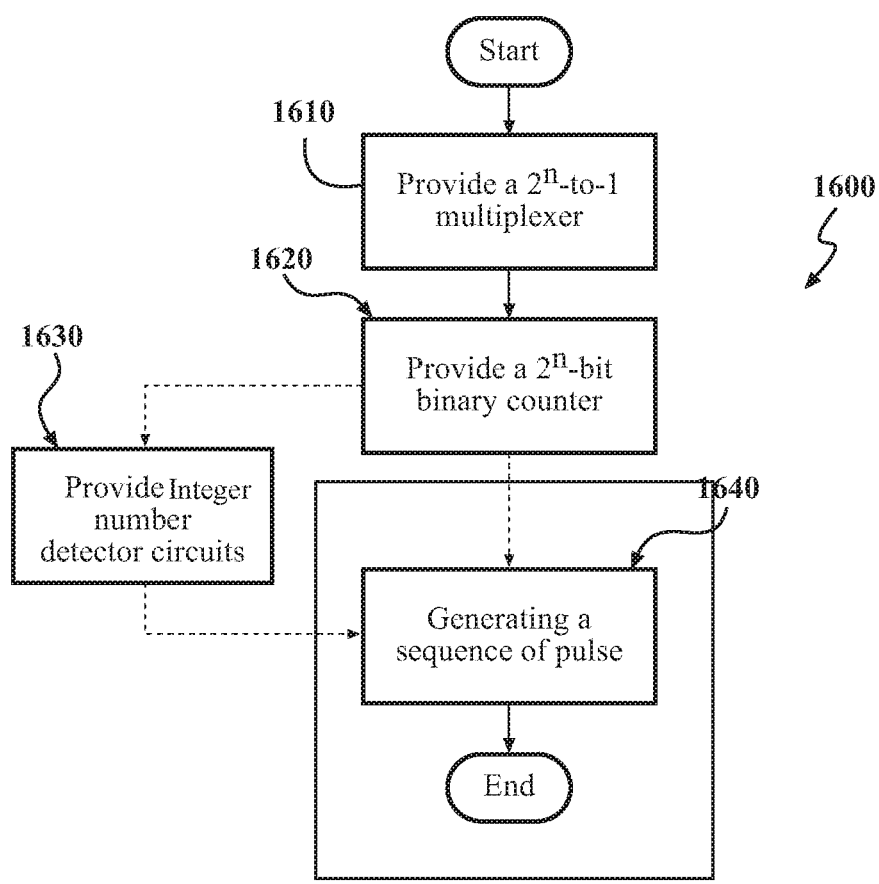
FIG. 16 is a flow diagram of methods to generate sequence of pulses.

Referring now to FIG. 16, a flow diagram is provided showing methods of generating odd or even numbers or a continuous sequence of pulses. An embodiment of method 1600 of generating a sequence of pulses, includes a plurality of steps. Step 1610 includes providing a $2^n$-to-1 multiplexer having $2^n$ input lines, n selector lines and an output line providing an output of the multiplexer, connecting one of the $2^n$ input lines to ground or zero potential, connecting the n selector lines to a selector signal, and the multiplexer selecting one of the $2^n$ input lines as the output of the multiplexer based on the selector signal.

Step 1620 includes providing a $2^n$-bit binary counter having a clock signal input line, a reset signal input line, a clock enable line, and $2^n$ output lines, connecting the clock signal input line to a clock signal input, connecting the reset signal input line to a reset signal input, connecting the clock enable line to the output line of the multiplexer for providing the output of the multiplexer as an input signal for the clock enable line, one of the $2^n$ output lines providing a sequence of pulse as an output of the transmit signal generator, and connecting each of the remaining $2^n$ output lines of the binary counter to one of the remaining $2^n$ input lines of the multiplexer. Step 1640 is then followed to generate a sequence of 1, 2, 4, 8, . . . n pulses. According to step 1640, the output of the transmit signal generator is providing a continuous pulse or an N pulse sequence as the output based on the selector signal and the reset signal input initiating generation of the sequence of pulses, wherein N≤$2^n$ and n is an integer.

If an odd number (i.e. 1, 3, 5, . . . n), another integer (e.g. 6, 12, 14; numbers that are not obtained by using power of 2) or a continuous number of pulses are to be generated, then the method 1600 is followed as discussed below. The numbers discussed above are identified herein as positive integer numbers. An embodiment of method 1600 for generating a positive integer number of pulses at 1610 includes the steps of providing a $2^n$-to-1 multiplexer having $2^n$ input lines, n selector lines and an output line providing an output of the multiplexer, connecting one of the $2^n$ input lines to ground or zero potential, and connecting the n selector lines to a selector signal, the multiplexer selecting one of the $2^n$ input lines as the output of the multiplexer based on the selector signal.

At 1620, the method includes providing a $2^n$ bit binary counter having a clock signal input line, a reset signal input line, a clock enable line, and $2^n$ output lines, connecting the clock signal input line to a clock signal input, connecting the reset signal input line to a reset signal input, connecting the clock enable line to the output line of the multiplexer providing the output of the multiplexer as an input signal for the clock enable line, one of the $2^n$ output lines providing a sequence of pulse as an output of the transmit signal generator, and connecting another of the $2^n$ output lines of the binary counter to one of the $2^n$ input lines of the multiplexer.

At 1630, the method includes providing ($2^n$-2) integer-number detector circuits and connecting each of the $2^n$ output lines of the binary counter to each of the integer-number detector circuits as an input, each of the integer-number detector circuits having an output line connected to one of the remaining $2^n$ input lines of the multiplexer. Integer-number detector circuits 1295, 1290 are discussed above in reference to FIG. 12. Integer-number detector circuits 1300, 1400 are discussed above in reference to FIGS. 13 and 14. At 1640, the method includes that the output of the transmit signal generator provides a continuous pulse or an N pulse sequence as the output based on the selector signal and the reset signal input initiating generation of the sequence of pulses, wherein N≤$2^n$, n is an integer and N is a positive integer number.

However, it should be understood that this is merely illustrative, and other arrangements of the ultrasound imaging system and transmit signal generator relative to the above discussed various components thereof are contemplated and included within the scope of the present disclosure.

The foregoing detailed description has been presented for purposes of illustration and description. It is not intended to be exhaustive or to limit embodiments to the precise form disclosed. Many modifications and variations are possible in light of the above teaching. The described embodiments were chosen in order to explain principles and practical applications, to thereby enable others skilled in the art to best utilize various embodiments and with various modifications as are suited to the particular use contemplated. It is intended that the scope be defined by the claims appended hereto.

The invention claimed is:

1. A transmit signal generator for generating a sequence of pulses, comprising:
   a $2^n$-to-1 multiplexer having $2^n$ input lines, one of the $2^n$ input lines being connected to ground or zero potential, n selector lines connected to a selector signal and an output line providing an output of the multiplexer, the multiplexer operable to select one of the $2^n$ input lines as the output of the multiplexer based on the selector signal; and
   a $2^n$-bit binary counter having a clock signal input line connected to a clock signal input, a reset signal input line connected to a reset signal input, a clock enable line connected to the output line of the multiplexer providing the output of the multiplexer as an input signal for the clock enable line, and $2^n$ output lines, one of the $2^n$ output lines providing a sequence of pulse as an output of the transmit signal generator and the remaining $2^n$ output lines of the binary counter each connected to one of the remaining $2^n$ input lines of the multiplexer;
   wherein the output of the transmit signal generator provides a continuous pulse or an N pulse sequence as the output based on the selector signal and the reset signal input initiating generation of the sequence of pulses, wherein $N \leq 2^n$ and n is an integer.

2. The transmit signal generator of claim 1, further comprising an inverter between the output line of the multiplexer and the clock enable line for inverting the output of the multiplexer and providing the inverted output as the input signal for the clock enable line of the binary counter.

3. The transmit signal generator of claim 1, wherein the one of the $2^n$ input lines connected to ground or zero potential is a least significant bit of the input lines of the multiplexer.

4. The transmit signal generator of claim 1, wherein the one of the $2^n$ output lines providing the sequence of pulses as the output is a least significant bit of the $2^n$ output lines of the binary counter.

5. The transmit signal generator of claim 1, wherein N is 1 or x, and $x=2^n$.

6. The transmit signal generator of claim 1, wherein the selector signal is set to 00, 01, 10 and 11 to provide the sequence of a continuous, single, two and four pulse output, respectively, as the output of the transmit signal generator.

7. The transmit signal generator of claim 1, wherein the clock signal input for the binary counter has a frequency of H Hz and the output of the transmit signal generator has a frequency of $H/2^n$ Hz.

8. The transmit signal generator of claim 1, wherein the binary counter is a $2^n$-bit frequency counter comprising $2^n$ Toggle flip-flop (T-FF) circuits and ($2^n$-2) AND gates.

9. The transmit signal generator of claim 8, wherein at least one of the T-FF circuits comprises a Data flip-flop (D-FF) circuit and an inverter.

10. The transmit signal generator of claim 8, wherein at least one of the T-FF circuits comprises a Data flip-flop (D-FF), two inverters, two AND gates and an OR gate.

11. An ultrasound imaging system, comprising the transmit signal generator of claim 1.

12. The transmit signal generator of claim 1, further comprising:
    at least one ($2^n$-2) integer-number detector circuit;
    each of the $2^n$ output lines of the binary counter connected to each of the at least one integer-number detector circuit as input; and
    each of the at least one integer-number detector circuit having an output line connected to one of the remaining $2^n$ input lines of the multiplexer, wherein N is a positive integer number.

13. The transmit signal generator of claim 12, wherein each of the at least one integer-number detector circuit comprise an AND gate and a plurality of inverters.

14. The transmit signal generator of claim 12, wherein the selector signal is set to 00, 01, 10 and 11 respectively to provide the sequence of a continuous, single, three and five pulse output as the output of the transmit signal generator.

15. A method of generating a sequence of pulses, comprising the steps of:
    providing a $2^n$-to-1 multiplexer having $2^n$ input lines, n selector lines and an output line providing an output of the multiplexer;
    connecting one of the $2^n$ input lines to ground or zero potential;
    providing a selector signal to the n selector lines for selecting one of the $2^n$ input lines of the multiplexer as the output of the multiplexer based on the selector signal;
    providing a $2^n$-bit binary counter having a clock signal input line, a reset signal input line, a clock enable line, and $2^n$ output lines;
    providing a clock signal input to the clock signal input line and a reset signal input to the reset signal input line; and
    providing an input signal for the clock enable line by connecting the clock enable line to the output line of the multiplexer, the binary counter providing an output signal based on the clock signal input, the reset signal input and the input signal for the clock enable line;
    wherein one of the $2^n$ output lines providing a sequence of pulse as an output of the transmit signal generator, each of the remaining $2^n$ output lines of the binary counter is connected to one of the remaining $2^n$ input lines of the multiplexer, the output of the transmit signal generator is providing a continuous pulse or an N pulse sequence as the output based on the selector signal and the reset signal input initiates generation of the sequence of pulses, wherein $N \leq 2^n$ and n is an integer.

16. The method of claim 15, further comprising:
    providing at least one ($2^n$-2) integer-number detector circuit; and
    connecting each of the $2^n$ output lines of the binary counter to each of the at least one integer-number detector circuit as input, each of the at least one integer-number detector circuit having an output line connected to one of the remaining $2^n$ input lines of the multiplexer, wherein N is a positive integer number.

* * * * *